US010667787B2

(12) United States Patent
Broad et al.

(10) Patent No.: US 10,667,787 B2
(45) Date of Patent: Jun. 2, 2020

(54) ULTRASOUND SYSTEM WITH DOCKING STATION AND DOCKABLE ULTRASOUND PROBE (71) Applicant: EchoNous, Inc., Bothell, WA (US)

(72) Inventors: Ron Broad, Arlington, WA (US); Todd Willsie, Seattle, WA (US); Greg Nieminen, Bothell, WA (US); Niko Pagoulatos, Kirkland, WA (US)

(73) Assignee: EchoNous, Inc., Redmond, WA (US)

( * ) Notice: Subject to any disclaimer, the term of this patent is extended or adjusted under 35 U.S.C. 154(b) by 468 days.

(21) Appl. No.: 15/446,290

(22) Filed: Mar. 1, 2017

(65) Prior Publication Data
US 2017/0252004 A1 Sep. 7, 2017

Related U.S. Application Data (60) Provisional application No. 62/302,109, filed on Mar. 1, 2016.

(51) Int. Cl.
*A61B 8/00* (2006.01)
*A61B 8/08* (2006.01)
*A61B 8/14* (2006.01)

(52) U.S. Cl.
CPC .......... *A61B 8/4433* (2013.01); *A61B 8/145* (2013.01); *A61B 8/4427* (2013.01);
(Continued)

(58) Field of Classification Search
CPC ......... A61B 8/4427; A61B 8/56; A61B 8/546; A61B 8/4433; A61B 2560/0456;
(Continued)

(56) References Cited

U.S. PATENT DOCUMENTS 5,564,424 A 10/1996 Yao
2003/0204140 A1* 10/2003 Ferek-Patric ...... A61N 1/36528
600/439
(Continued)

FOREIGN PATENT DOCUMENTS

WO 2004/080364 A2 9/2004
WO 2013/148730 A2 10/2013

OTHER PUBLICATIONS

Zhou et al., Frequency Accuracy & Stability Dependencies of Crystal Oscillators, Nov. 2008 (Year: 2008).*
(Continued)

*Primary Examiner* — Amelie R Davis
(74) *Attorney, Agent, or Firm* — Seed Intellectual Property Law Group LLP (57) ABSTRACT An ultrasound system comprising a portable ultrasound probe and a docking station provides enhanced ultrasound functionality. One or more first transducer elements transmit an ultrasound signal toward a target structure in a region of interest. Processing circuitry controls transmission of the ultrasound signal, while driving circuitry that is operatively coupled to the one or more first transducer elements and the processing circuitry drives the transmission of the ultrasound signal. The ultrasound probe further includes one or more second transducer elements that receive echo signals returning from the target structure in response to transmission of the ultrasound signal, and a power supply that provides power to the driving circuitry for transmission of the ultrasound signal. The docking station includes an interface that is couplable to the ultrasound probe and circuitry that electrically couples to the ultrasound probe via the interface and enhances the ultrasound functionality of the ultrasound probe.

38 Claims, 5 Drawing Sheets (52) U.S. Cl.
CPC ............ *A61B 8/4494* (2013.01); *A61B 8/467* (2013.01); *A61B 8/5246* (2013.01); *A61B 8/5269* (2013.01); *A61B 8/546* (2013.01); *A61B 8/56* (2013.01)

(58) Field of Classification Search
CPC ... A61B 8/4405; A61B 8/4472; A61B 8/4411; A61B 8/4488; A61B 8/54; A61B 2560/045; A61B 8/488; A61B 8/145; A61B 8/4494; A61B 8/467; A61B 8/5246; A61B 8/5269; G01S 15/899; G01S 15/8979; G01S 7/5208; G01S 7/52082; G01S 15/8915; G01S 7/52079; G01S 7/52046; G01S 7/52096; G01S 7/52077; G06F 1/1632; F28D 15/0266; F28D 15/0275
See application file for complete search history.

(56) References Cited

U.S. PATENT DOCUMENTS

| | | | |
|---|---|---|---|
| 2004/0158148 A1* | 8/2004 | Amemiya | B06B 1/0215 600/437 |
| 2004/0179332 A1* | 9/2004 | Smith | A61B 8/00 361/679.41 |
| 2006/0094960 A1* | 5/2006 | Phung | G01S 7/52017 600/437 |
| 2006/0191344 A1* | 8/2006 | Hashimoto | A61B 8/00 73/632 |
| 2007/0276252 A1* | 11/2007 | Kolasa | A61B 8/06 600/459 |
| 2008/0055826 A1 | 3/2008 | Smith et al. | |
| 2009/0150692 A1* | 6/2009 | Poland | G06F 1/3287 713/320 |
| 2009/0224611 A1 | 9/2009 | Chen | |
| 2012/0101389 A1* | 4/2012 | Tanabe | A61B 8/4472 600/459 |
| 2012/0265027 A1 | 10/2012 | Lee et al. | |
| 2014/0350357 A1* | 11/2014 | Lee | A61B 8/4227 600/301 |
| 2015/0289853 A1 | 10/2015 | Cho et al. | |
| 2015/0327839 A1 | 11/2015 | Kim et al. | |

OTHER PUBLICATIONS

International Search Report and Written Opinion for Application No. PCT/US2017/020264 dated May 11, 2017, 15 pages.
Extended Supplementary European Search Report for European Application No. 17 76 0745, dated Aug. 2, 2019, 6 pages.

* cited by examiner

ULTRASOUND SYSTEM WITH DOCKING STATION AND DOCKABLE ULTRASOUND PROBE

BACKGROUND

Technical Field

The present application pertains to ultrasound systems, and more particularly to ultrasound systems with portable handheld ultrasound probes for visualization and evaluation of target structures in a region of interest.

Description of the Related Art

Ultrasound imaging is a useful as an imaging modality in a number of environments. For example, in the field of healthcare, internal structures of a patient's body may be imaged before, during or after a therapeutic intervention. A healthcare professional may hold a portable ultrasound probe, or transducer, in proximity to the patient and move the transducer as appropriate to visualize one or more target structure(s) in a region of interest in the patient. A transducer may be placed on the surface of the body or, in some procedures, a transducer is inserted inside the patient's body. The healthcare professional coordinates the movement of the transducer so as to obtain a desired representation on a screen, such as a two-dimensional cross section of a three-dimensional volume.

Ultrasound may also be used to measure functional aspects of a patient, such as organ movement and blood flow in the patient. Doppler measurements, for example, are effective in measuring the direction and speed of movement of a structure, such as a heart valve or blood cells flowing in a vessel, relative to the transducer. Doppler echocardiography is widely used for evaluating the cardiocirculatory system of patients with known or suspected cardiovascular disease.

For many years, ultrasound imaging was effectively confined to large equipment operating in a hospital environment. Recent technological advances, however, have produced smaller ultrasound systems that increasingly are deployed in frontline point-of-care environments, e.g., doctor's offices. Nevertheless, smaller ultrasound systems typically lack the power, thermal management, and processing capabilities of larger systems. This generally results in limited runtime of the ultrasound imaging components, lower image resolution, and fewer features or modes of operation.

BRIEF SUMMARY

The present application, in part, addresses a desire for smaller ultrasound systems, having greater portability, lower cost, and ease of use for different modes of ultrasound imaging, while at the same time providing high quality measurements and effective thermal management.

In at least one embodiment, an ultrasound system comprises an ultrasound probe and a docking station. The ultrasound probe is preferably a portable ultrasound probe, such as the handheld probe, that includes one or more first transducer elements that transmit an ultrasound signal toward a target structure in a region of interest. The ultrasound probe also includes processing circuitry that controls transmission of the ultrasound signal from the one or more first transducer elements and driving circuitry operatively coupled to the one or more first transducer elements and the processing circuitry. The driving circuitry drives the transmission of the ultrasound signal by the one or more first transducer elements in response to a control signal received from the processing circuitry. The ultrasound probe further includes one or more second transducer elements that receive echo signals returning from the target structure in response to transmission of the ultrasound signal, and a power supply that provides power to the driving circuitry for transmission of the ultrasound signal in at least a pulsed wave mode of operation.

The docking station includes an interface that is couplable to the ultrasound probe. The docking station also includes circuitry that electrically couples to the ultrasound probe via the interface and enhances the ultrasound functionality of the ultrasound probe. In at least one embodiment, the docking station is provided separate from the ultrasound probe. In various embodiments, the circuitry in the docking station enhances the ultrasound functionality of the ultrasound probe by employing higher-quality components, such as a power supply, oscillator, and/or heat dissipation elements or by providing greater computational resources for generating, receiving, and/or processing ultrasound signals or data.

In yet another embodiment, described herein is a method for transmitting an ultrasound signal from a handheld ultrasound probe. The method includes positioning the ultrasound probe with respect to a target structure in a region of interest; operating the ultrasound probe in a first mode of operation or a second mode of operation, wherein in the first mode of operation, one or more first transducer elements in the ultrasound probe transmit a pulsed wave ultrasound signal toward the target structure and one or more second transducer elements receive an echo signal returning from the target structure, and in the second mode of operation, the one or more first transducer elements in the ultrasound probe transmit a continuous wave ultrasound signal toward the target structure while the one or more second transducer elements receive echo signals returning from the target structure. The method further includes coupling the ultrasound probe to a separate docking station having circuitry that enhances operation of the ultrasound probe in the first mode of operation or the second mode of operation.

DETAILED DESCRIPTION

With Doppler echocardiography, an ultrasound transducer transmits a high frequency ultrasound signal, typically in the range of 2 to 5 MHz, toward a target structure in a region of interest. In a healthcare environment, the target structure may be, for example, blood cells in a blood vessel or a heart valve in a chamber of the heart. The ultrasound transducer then receives one or more echo signals in return and determines the difference in frequency of the transmitted signal and the received echo signal. The difference in frequency relates to the velocity and direction of movement of the structures such as the blood cells, heart valves, etc., within the region of interest.

Doppler measurements may be performed using continuous and/or pulsed modalities, each having their own advantages and disadvantages. Systems providing pulsed wave Doppler transmit ultrasound pulses at a frequency called the pulse repetition frequency (PRF). An advantage of pulsed ultrasound systems is that the ultrasound pulses and their corresponding echoes provide information about the depth or range of a measured structure in the region of interest.

Typically low velocities, for example the flow of blood in veins, are measured using low pulse repetition frequencies, while high velocities, for example the flow of blood in arteries, are measured using higher pulse repetition frequencies. Nevertheless, pulsed wave Doppler imaging suffers from aliasing if the velocity of the measured structure and the angle between the ultrasound beam and the direction of movement of the measured structure result in a frequency greater than half of the pulse repetition frequency, i.e., the "Nyquist limit." Additionally, with pulsed systems, the depth of measurement is limited by the pulse repetition frequency. Range gating using a timing mechanism samples the returning echo signals from only a given region of interest.

Generally, it is desirable to use as high a PRF as possible for recording abnormally elevated velocities. Setting a high PRF, however, is limited by the distance from the transducer to the target structure in the region of interest. Sufficient time is needed for the pulse to travel from the transducer to the measured structure and back to the transducer, before transmission of the next pulse. The closer the sample volume is located to the transducer, the higher the maximum PRF that can be used. Conversely, the farther away the target structure, the lower the maximum PRF becomes. Pulsed wave Doppler is primarily used to evaluate velocities across normal cardiac valves or blood vessels to evaluate function or blood flow.

Continuous wave Doppler systems use a transducer with one or more transducer elements that continuously transmit ultrasound signals and one or more other transducer elements that continuously receive reflected echo signals. This modality provides the ability to record higher blood flow velocities since the measurements are not affected by the Nyquist limit. Continuous wave Doppler, however, does not allow precise localization of the velocities that are measured along the ultrasound beam path. Continuous wave Doppler is typically used for measuring high velocities across obstructed and/or regurgitant lesions, for example.

Generally, when a healthcare professional wants to know where a specific area of abnormal flow is located, a pulsed wave Doppler is indicated. When an accurate measurement of elevated flow velocity is required, continuous wave Doppler is used. Hence, in many cases, a combination of pulsed wave and continuous wave Doppler is used to determine both velocity and location of a particular structure or blood flow jet of interest.

Described herein is an ultrasound system that includes a portable ultrasound probe capable of performing at least pulsed wave Doppler measurements when the ultrasound probe is in an "undocked" state or configuration. The ultrasound system further includes a docking station with additional circuitry that enhances the ultrasound functionality of the ultrasound probe when the ultrasound probe is "docked" or coupled to the docking station. For example, when the ultrasound probe is coupled to the docking station (i.e., in a "docked" state or configuration), the circuitry in the docking station may add continuous wave Doppler functionality or provide enhanced pulsed wave or continuous wave Doppler using the same transducer of the ultrasound probe. The ultrasound system gives the user of the ultrasound probe the option of adding to and/or improving upon the ultrasound functionality of the ultrasound probe by coupling the ultrasound probe to the docking station.

Figure 1:
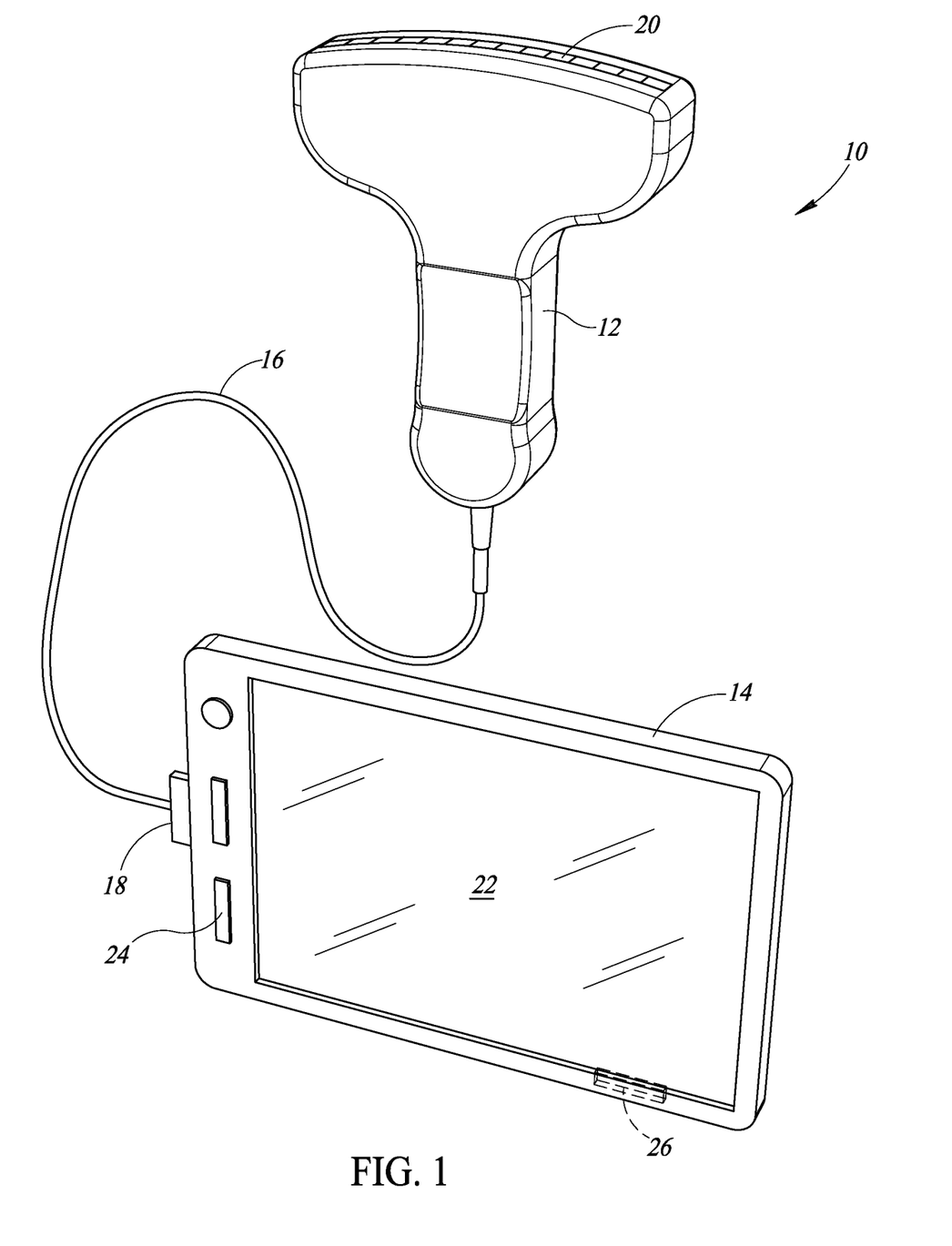
FIG. 1 is a pictorial diagram of an ultrasound probe in accordance with one or more embodiments of the present disclosure.
Figure 2:
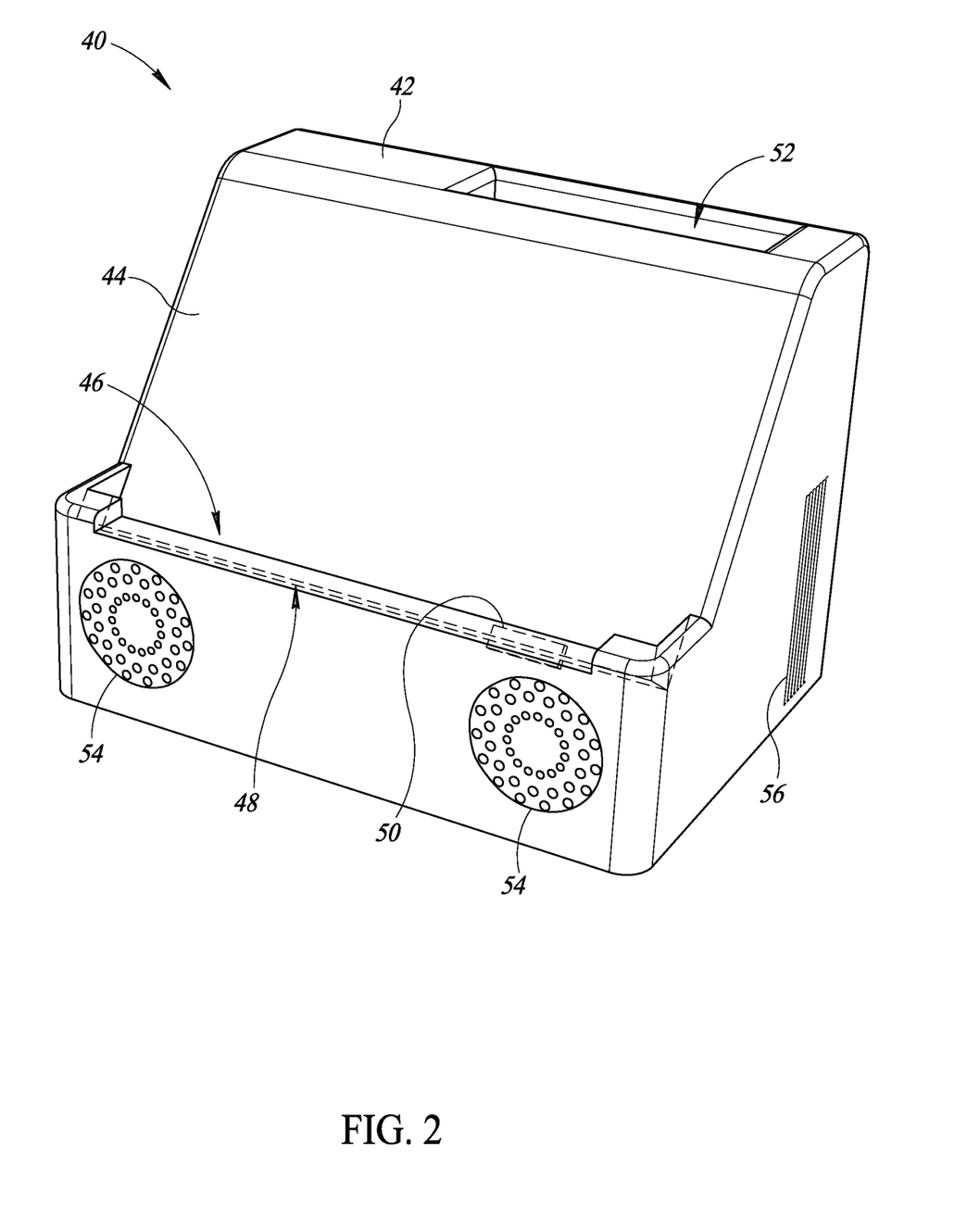
FIG. 2 is a pictorial diagram of a docking station in accordance with one or more embodiments of the present disclosure.
Figure 3:
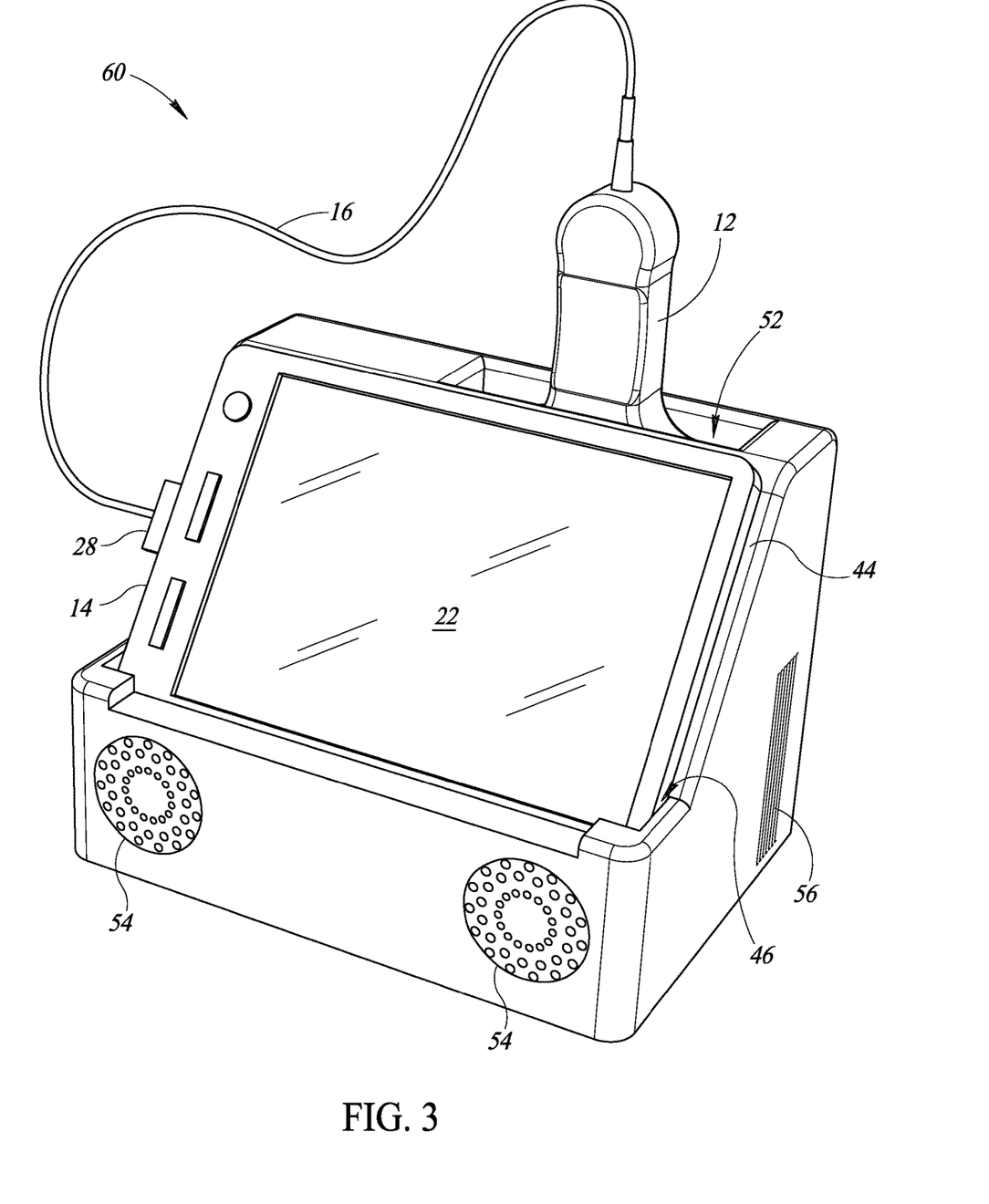
FIG. 3 is a pictorial diagram of the ultrasound probe of FIG. 1 coupled to the docking station of FIG. 2 in accordance with one or more embodiments of the present disclosure.

FIG. 1 provides a pictorial diagram of a portable ultrasound probe 10 constructed in accordance with one or more embodiments of the present disclosure. The ultrasound probe 10 includes a transducer 12 that is electrically coupled to a computing device 14 by a cable 16. The cable 16 includes a connector 18 that detachably connects the transducer 12 to the computing device 14. As will be described further below, the ultrasound probe 10 may be coupled to a docking station (e.g., as shown in FIG. 2). In some embodiments, coupling of the ultrasound probe 10 to a docking station includes detaching the transducer 12 from the computing device 14 and using the connector 18 to directly connect the transducer 12 to the docking station. In other embodiments, when the ultrasound probe 10 is coupled to a docking station, the transducer 12 remains connected to the computing device 14 (e.g., as shown in FIG. 3), and the computing device 14 is coupled to the docking station.

The transducer 12 is configured to transmit an ultrasound signal toward a target structure in a region of interest. The transducer 12 is further configured to receive echo signals returning from the target structure in response to transmission of the ultrasound signal. To that end, the transducer 12 includes transducer elements 20 that are capable of transmitting an ultrasound signal and receiving subsequent echo signals. In various embodiments, the transducer elements 20 may be arranged as elements of a phased array transducer. Suitable phased array transducers are known in the art.

As will be described in greater detail in connection with FIG. 4, the ultrasound probe 10 further includes processing circuitry and driving circuitry. In part, the processing circuitry controls the transmission of the ultrasound signal from the transducer elements 20. The driving circuitry is operatively coupled to the transducer elements 20 for driving the transmission of the ultrasound signal. The driving circuitry may drive the transmission of the ultrasound signal in response to a control signal received from the processing circuitry. The ultrasound probe 10 also includes a power supply that provides power to the driving circuitry for transmission of the ultrasound signal in at least a pulsed wave mode of operation.

The computing device 14 shown in FIG. 1 includes a display screen 22 and a user interface 24. The display screen 22 may use any type of display technology including, but not limited to, an LED technology. The display screen 22 is used to display one or more images generated from echo data obtained from the echo signals received in response to transmission of an ultrasound signal. In some embodiments, the display screen 22 may be a touch screen capable of receiving input from a user that touches the screen. In some embodiments, the user interface 24 may include one or more buttons, knobs, switches, and the like, capable of receiving input from a user of the ultrasound probe 10.

The computing device 14 further includes a docking station interface 26 that connects to a corresponding ultrasound probe interface on a docking station when the ultrasound probe 10 is coupled to the docking station. The docking station interface 26 may be constructed as a female connector that receives a corresponding male connector of the docking station and electrically couples circuitry in the docking station to circuitry in the computing device 14.

FIG. 2 is a pictorial diagram of a docking station 40 constructed in accordance with one or more embodiments of the present disclosure. The docking station 40 includes a housing 42 having a front surface 44 and a receiving section 46. In some embodiments, as illustrated in FIG. 3, an ultrasound probe 10 as illustrated in FIG. 1 may be coupled to the docking station 40 by sliding the computing device 14 of the ultrasound probe 10 along the front surface 44 into the receiving section 46. When docked as shown in FIG. 3, the computing device 14 of the ultrasound probe 10 rests on a bottom edge 48 of the receiving section 46. The docking station 40 includes an ultrasound probe interface 50 that is couplable to the ultrasound probe 10. In the illustrated embodiment, the ultrasound probe interface 50 electrically couples the docking station 40 to the corresponding docking station interface 26 of the computing device 14. FIG. 3 thus illustrates an ultrasound system 60 in which the ultrasound probe 10 of FIG. 1 is coupled to the docking station 40 of FIG. 2 in accordance with one or more embodiments of the present disclosure.

Figure 4:
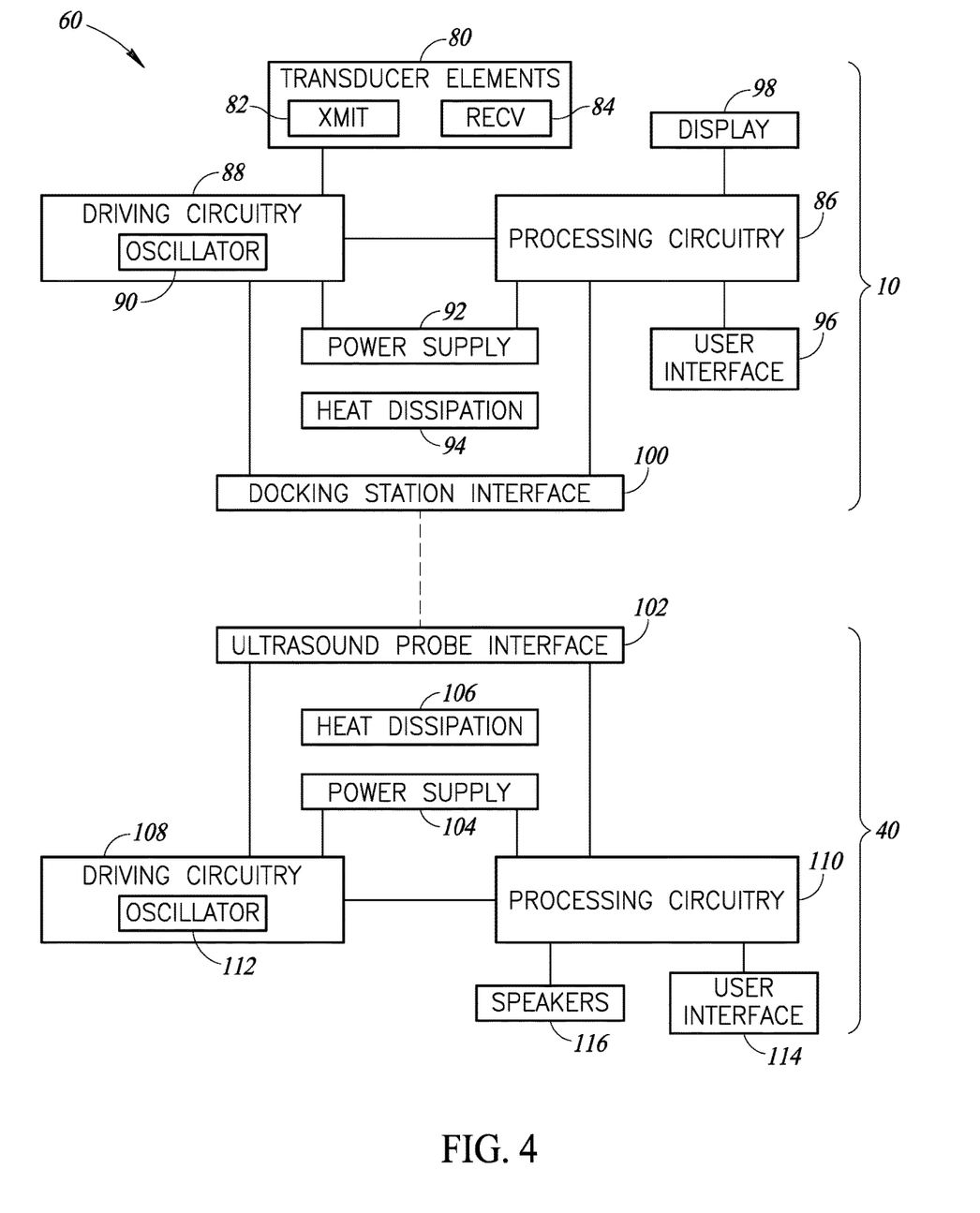
FIG. 4 is a block diagram of components of an ultrasound system including an ultrasound probe and a docking station in accordance with one or more embodiments of the present disclosure.

FIG. 4 is a block diagram of components of the ultrasound system 60 including the ultrasound probe 10 and the docking station 40. In FIG. 4, the ultrasound probe 10 includes transducer elements 80 (e.g., transducer elements 20 shown in FIG. 1) configured for transmission of an ultrasound signal toward a target structure in a region of interest. The transducer elements 80 include one or more first transducer elements 82 that transmit the ultrasound signal and one or more second transducer elements 84 that receive echo signals returning from the target structure in response to transmission of the ultrasound signal.

The ultrasound probe 10 further includes processing circuitry 86 coupled to driving circuitry 88. In various embodiments, the processing circuitry 86 includes one or more programmed processors that operate in accordance with computer-executable instructions that, in response to execution, cause the programmed processor(s) to perform various actions. For example, the processing circuitry 86 may be configured to send one or more control signals to the driving circuitry 88 to control the transmission of an ultrasound signal by the ultrasound probe 10.

The driving circuitry 88 may include an oscillator 90 that is used when generating an ultrasound signal to be transmitted by the one or more first transducer elements 82. The oscillator 90 is used by the driving circuitry 88 to generate and shape the ultrasound pulses that form the ultrasound signal.

The ultrasound probe 10 includes a power supply 92 that is electrically coupled to component parts of the ultrasound probe 10 including, but not limited to, the processing circuitry 86 and the driving circuitry 88. The power supply 92 provides power for operating the processing circuitry 86 and the driving circuitry 88. In particular, the power supply 92 provides power for generating the ultrasound signal by the driving circuitry 88 and transmitting the ultrasound signal, with stepped-up voltage as needed, by the one or more first transducer elements 82. The power provided by the power supply 92 also provides power for the driving circuitry 88 and the processing circuitry 86 when receiving echo signals via the one or more second transducer elements 84.

The docking station 40 shown in FIG. 3 further includes audio speakers 54 that may be used to generate audible representations of echo signals or other features derived from operation of the ultrasound probe 10. The docking station 40 also includes a grate 56 through which fans in the docking station 40 may blow air to expel heat generated by the components of the docking station 40.

During operation, components of the ultrasound probe 10, including but not limited to the power supply 92, generate heat that must be dissipated by the ultrasound probe 10. Accordingly, the ultrasound probe 10 may include one or more heat dissipation elements 94 configured to draw away and dissipate heat from the components of the ultrasound probe 10. For example, the heat dissipation elements 94 may include one or more thermal circuits that are thermally coupled to the components of the ultrasound probe 10, including the power supply 92, and conduct heat toward a surface of the ultrasound probe 10 for dissipation by conduction to a user's hand and/or convection to the surrounding environment.

The processing circuitry 86 is further coupled to a user interface 96 and a display 98. In at least one embodiment, the display 98 may comprise the screen 22 described with respect to FIG. 1, while the user interface 96 may comprise the interface elements 24 described with respect to FIG. 1.

The processing circuitry 86 and the driving circuitry 88 of the ultrasound probe 10 are further electrically coupled to a docking station interface 100. The docking station interface 100 may comprise the interface 26 described with respect to FIG. 1. As shown in FIG. 4, the docking station interface 100 may be coupled to a corresponding ultrasound probe interface 102 of the docking station 40 when the ultrasound probe 10 is docked with the docking station 40.

The docking station 40 includes a power supply 104 that provides power for generating an ultrasound signal by driving circuitry 108 in the docking station 40. The power supply 104 also provides power for processing circuitry 110 in the docking station 40. As with the driving circuitry 88 in the ultrasound probe 10, the driving circuitry 108 in the docking station 40 may include an oscillator 112 that is used by the docking station 40 when generating an ultrasound signal to be transmitted by the one or more first transducer elements 82 of the ultrasound probe 10. As will be described in greater below, the power supply 104 and/or the oscillator 112 of the docking station 40 may be comprised of higher-quality components that ultimately enhance the ultrasound signal that is transmitted and/or received by the ultrasound probe 10.

During operation, components of the docking station 40, including but not limited to the oscillator 112 and the power supply 104, generate heat that must be dissipated by the docking station 40. Accordingly, the docking station 40 includes one or more heat dissipation elements 106 that are configured to draw heat away from the components of the docking station 40 and dissipate the heat. For example, the heat dissipation elements 106 may include, for example, one or more thermal circuits with heat pipes that are thermally coupled to the components of the docking station 40. The thermal circuits or other thermally-conductive connections conduct heat toward an element capable of dissipating the heat, e.g., a surface that uses convection to dissipate heat to a surrounding environment. For example, the heat dissipation elements 106 may include a thermally conductive structure with fins that provide increased surface area for dissipating heat. One or more fans may be used in the docking station 40 to provide forced convection of the heat. As illustrated in FIGS. 2 and 3, the docking station 40 may include a grate 56 through which the fan(s) in the docking station 40 may blow air to expel heat generated by the components of the docking station 40. In various embodiments, the power supply 104 is thermally coupled to a heat dissipation element 106 that provides greater heat dissipation than a heat dissipation element 94 that is thermally coupled to the power supply 92 in the ultrasound probe 10.

In the embodiment shown in FIG. 4, the processing circuitry 110 is further coupled to a user interface 114 and audio speakers 116. In at least one embodiment, the speakers 116 may comprise the audio speakers 54 described with respect to FIGS. 2 and 3. The user interface 114 may comprise one or more buttons, knobs, switches, and the like, to receive user input for directing the operation of the docking station 40 and possibly the ultrasound probe 10 when the ultrasound probe 10 is coupled to the docking station 40.

As mentioned above, the docking station 40 includes circuitry that, when electrically coupled to the ultrasound probe 10 via the ultrasound probe interface 102, enhances the ultrasound functionality of the ultrasound probe 10. In at least one embodiment, the circuitry in the docking station 40 includes driving circuitry 108 that is operatively coupled to the transducer elements 80 of the ultrasound probe 10. The driving circuitry 108 may be configured to drive the transmission of an ultrasound signal by the one or more first transducer 82, and may also be configured to receive echo signals from the one or more second transducer elements 84 that result from transmission of the ultrasound signal. The driving circuitry 108 may be operatively coupled to the processing circuitry 86 in the ultrasound probe 10 to receive control signal(s) from the processing circuitry 86 and/or the driving circuitry 108 may be operatively coupled to the processing circuitry 110 in the docking station 40 to receive control signal(s), e.g., for operation of the ultrasound system 60.

In various embodiments, the circuitry in the docking station 40 enhances the ultrasound functionality of the ultrasound probe 10 by using a higher-quality oscillator 112 in the driving circuitry 108. In at least one embodiment, a higher-quality oscillator 112 introduces less noise into the ultrasound signal than an oscillator (e.g., oscillator 90) in the driving circuitry 88 of the ultrasound probe 10 that is otherwise used by the ultrasound probe 10 when the ultrasound probe 10 is not coupled to the docking station 40. The oscillator 112 may be more stable, jitter free, less noisy over a wider bandwidth, and/or have a more optimal slew rate as compared to the oscillator 90. The oscillator 112 may act separate from and/or replace the use of the oscillator 90 when the ultrasound probe 10 is docked with the docking station 40. In other embodiments, the oscillator 112 may operate in conjunction with the oscillator 90 when generating the ultrasound signal. In at least one such embodiment, the oscillator 90 provides a reference frequency for synchronizing operation of the oscillator 112.

In various embodiments, the circuitry in the docking station 40 enhances the ultrasound functionality of the ultrasound probe 10 by using a higher-quality power supply 104. In such embodiments, the power supply 94 in the ultrasound probe 10 is a first power supply that provides power for generating and transmitting the ultrasound signal when the ultrasound probe 10 is not coupled to the docking station 40. When the ultrasound probe 10 is coupled to the docking station 40, the power supply 104 is a second power supply that provides power for generating and transmitting the ultrasound signal, either in conjunction with or in place of the power supply 94. In at least one embodiment when the ultrasound probe 10 is coupled to the docking station 40, driving circuitry 108 in the docking station 40 is electrically coupled to the ultrasound probe 10 via the interface 102 and uses the power provided by the second power supply 104 to transmit the ultrasound signal, e.g., in a continuous wave mode of operation. One example of a higher-quality power supply 104 is a power supply that introduces less electrical noise into the ultrasound signal than power that is otherwise provided by the first power supply 92 when the ultrasound probe 10 is not coupled or docked with the docking station 40. Higher quality power supplies generally consume more power and produce more heat due to the additional or improved filtering that is used when producing a higher quality or cleaner power signal.

The processing circuitry 110 in the docking station 40 may detect when the ultrasound probe 10 is coupled to the docking station 40. Subsequent to detecting that the ultrasound probe 10 is coupled to the docking station 40, the processing circuitry 110 (or a portion thereof) controls transmission of the ultrasound signal from the one or more first transducer elements 82. In some embodiments, the processing circuitry 110 may act to control the driving circuitry 108 and/or the driving circuitry 88 such that the ultrasound probe 10 transmits the ultrasound signal and receives echo signals in a continuous wave mode of operation. The ultrasound probe 10 may further include a user interface (e.g., one or more aspects of user interface 96 shown in FIG. 4) that receives a user actuation of the ultrasound probe 10. When the ultrasound probe 10 is coupled to the docking station 40, the user actuation may determine whether the ultrasound probe 10 transmits the ultrasound signal in a pulsed wave mode of operation or a continuous wave mode of operation.

As mentioned earlier, the docking station 40 includes at least one receiving section for holding the ultrasound probe 10 when the ultrasound probe 10 is coupled to the docking station 40. In embodiments where the ultrasound probe 10 includes a transducer 12 electrically coupled to a computing device 14 as shown in FIG. 1, the docking station 40 may include multiple receiving sections as shown in FIGS. 2 and 3. For example, the docking station 40 may include a first receiving section 46 configured to hold the computing device 14. The first receiving section 46 may include a heat dissipating interface, such as the front surface 44, that thermally couples to the computing device 14 when the ultrasound probe 10 is coupled to the docking station 40 and conveys heat away from the computing device 14.

The docking station 40 may further include a second receiving section 52 configured to hold the transducer 12. The second receiving section 52 may include a heat dissipating interface (e.g. a liner of the receiving section 52) that thermally couples to the transducer 12 and conveys heat away from the transducer 12 when the transducer 12 is placed in the second receiving section 52. Active components, such as fans and/or heat pipes, may be used to conduct heat away from the transducer 12 and/or the computing device 14 as well as the heat-producing components of the docking station 40. The multiple receiving sections 46 and 52 are thus configured to hold different portions of the ultrasound probe 10 when the ultrasound probe 10 is coupled to the docking station 40.

In some embodiments, to reduce the heat generated by the ultrasound probe 10 when the ultrasound probe 10 is not coupled to the docking station 40 (and thus is not able to take advantage of the greater heat dissipation capabilities of the docking station 40), the ultrasound probe may be configured to limit the transmission of an ultrasound signal in a continuous wave mode of operation to shorter periods of time than when the ultrasound probe 10 is coupled to the docking station 40. In yet other embodiments, when the ultrasound probe 10 is not coupled to the docking station 40, the ultrasound probe 10 may be configured such that it does not transmit an ultrasound signal in a continuous wave mode of operation.

In various embodiments, the circuitry in the docking station 40 enhances the ultrasound functionality of the ultrasound probe 10 by using processing circuitry 110 that provides a greater computational resource for processing echo signals received in response to transmission of an ultrasound signal by the ultrasound probe 10. Generally, faster processors capable of performing more computationally-intensive algorithms generate more heat. However, better imagery with higher resolution may be obtained by applying more computationally-intensive algorithms to process the received echo signals. With the greater heat dissipation capacity of the docking station 40, the docking station 40 may employ processing circuitry 110 that provides a greater computational resource (e.g., faster processor speed, greater number of processing cores, faster onboard memory, parallel processing architecture, etc.) when processing echo signals and generating images on the display screen 22 of the ultrasound probe 10.

The circuitry in the docking station 40 may also enhance the ultrasound functionality of the ultrasound probe 10 by using one or more higher-quality audio speakers 116 that have a better frequency response than audio speakers that may otherwise be included in the ultrasound probe 10. Additionally, the docking station 40 may employ audio codecs that require greater computational resources to provide enhanced auscultation of heart sounds and/or provide higher fidelity representations of aspects of the returning echo signals through the speakers 116.

Figure 5:
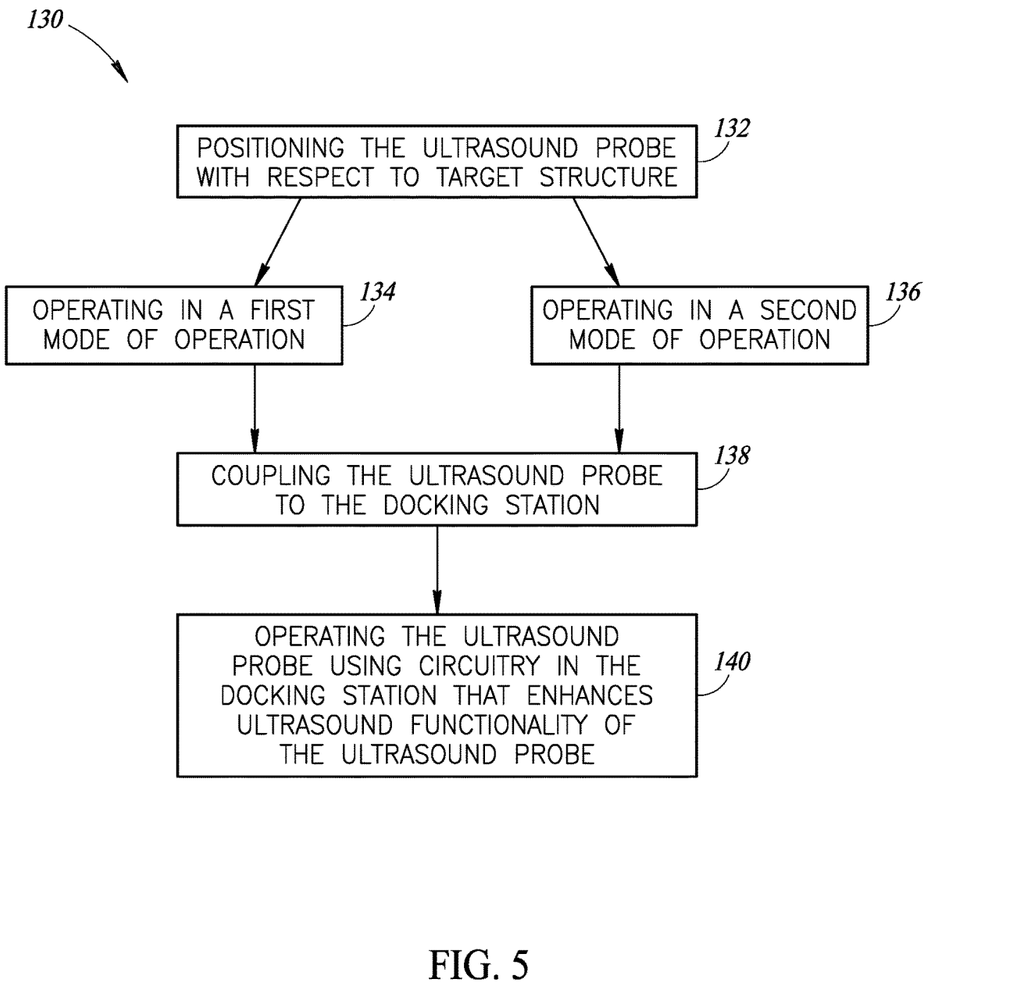
FIG. 5 is a flow diagram of operation of an ultrasound system in accordance with one or more embodiments of the present disclosure.

FIG. 5 is a flow diagram of a method of operation of an ultrasound system 60 in accordance with one or more embodiments of the present disclosure. In at least one embodiment, the method 130 includes positioning a handheld ultrasound probe 10 with respect to a target structure in a region of interest to be measured by the ultrasound probe 10, as indicated at block 132. Thereafter, the method 130 includes operating the ultrasound probe 10 in a first mode of operation 124 or a second mode of operation 136. In the first mode of operation 134, one or more first transducer elements in the ultrasound probe (e.g., elements 82 in FIG. 4) transmit a pulsed wave ultrasound signal toward the target structure and one or more second transducer elements (e.g., elements 84 in FIG. 4) receive an echo signal returning from the target structure. In the second mode of operation 136, the one or more first transducer elements 82 transmit a continuous wave ultrasound signal toward the target structure while the one or more second transducer elements 84 receive echo signals returning from the target structure. The method 130 further includes coupling the ultrasound probe to a separate docking station having circuitry that enhances the ultrasound functionality of the ultrasound probe in the first mode of operation 134 or the second mode of operation 136, as indicated at block 138. The method 130 thereafter includes operating the ultrasound probe using circuitry in the docking station that enhances the ultrasound functionality of the ultrasound probe, as indicated at block 140.

For example, in various embodiments as discussed above, the circuitry in the docking station may include a power supply that provides quieter power for transmission of an ultrasound signal as compared to power provided by a power supply in the ultrasound probe that otherwise powers the transmission of the ultrasound signal when the ultrasound probe is not coupled to the docking station. In some embodiments, the power provided by power supply in the docking station is quieter in that it introduces less electrical noise into the ultrasound signal than the power provided by a power supply in the ultrasound probe. Alternatively or in addition, the power supply in the docking station may be coupled to a heat dissipation element that provides greater heat dissipation than a heat dissipation element coupled to the power supply in the ultrasound probe.

The processing circuitry in the docking station may be configured to detect when the ultrasound probe and the docking station are in a docked state (i.e., when the ultrasound probe is coupled to the docking station). When a docked state is detected, the method may include controlling the circuitry in the docking station such that the ultrasound probe transmits a continuous wave ultrasound signal in the second mode of operation using power provided by the power supply in the docking station. Alternatively or in addition, when a docked state is detected, the circuitry in the docking station may be controlled such that the ultrasound probe transmits a pulsed wave ultrasound signal in the first mode of operation using power provided by the power supply in the docking station.

As noted earlier, coupling of the ultrasound probe to the docking station may include placing at least a portion of the ultrasound probe in a receiving section of the docking station. The receiving section may including a heat dissipating interface that thermally couples to ultrasound probe and conveys heat away from the ultrasound probe when the ultrasound probe is coupled to the docking station. In some embodiments as earlier mentioned, the docking station may include at least a first receiving section that is separate from a second receiving section. In such embodiments, the method may further comprise placing a portion of the ultrasound probe (such as the computing device 14) in the first receiving section and placing another portion of the ultrasound probe (such as the transducer 12) in the second receiving section.

The circuitry in the docking station may include driving circuitry with an oscillator that operatively couples to one or more transducer elements of the ultrasound probe when the ultrasound probe is coupled to the docking station. In such embodiments, the method may further comprise using the oscillator of the docking station when driving the transmission of the ultrasound signal in the first or second mode of operation. The oscillator may enhance the transmission of the ultrasound signal by introducing less noise into the ultrasound signal than an oscillator in the ultrasound probe that is otherwise used by the ultrasound probe when driving the ultrasound signal in an undocked state.

As may be appreciated by persons having ordinary skill in the art, aspects of the various embodiments described above can be combined to provide further embodiments. Aspects of the embodiments can also be modified, if necessary, to employ concepts of various patents, applications and publications in the relevant art to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An ultrasound system comprising:
    a portable ultrasound probe that includes:
        one or more first transducer elements that transmit an ultrasound signal toward a target structure in a region of interest;
        processing circuitry that controls transmission of the ultrasound signal from the one or more first transducer elements;
        driving circuitry operatively coupled to the one or more first transducer elements and the processing circuitry, wherein the driving circuitry drives the transmission of the ultrasound signal by the one or more first transducer elements in response to a control signal received from the processing circuitry;
        one or more second transducer elements that receive echo signals returning from the target structure in response to transmission of the ultrasound signal; and
        a power supply that provides power to the driving circuitry for transmission of the ultrasound signal in at least a pulsed wave mode of operation; and
    a docking station that includes:
        an electrical connector that is couplable to the ultrasound probe; and
        circuitry that electrically couples to the ultrasound probe via the electrical connector and enhances the ultrasound functionality of the ultrasound probe,
    wherein the circuitry in the docking station includes driving circuitry, and when the ultrasound probe is coupled to the docking station, the driving circuitry of the docking station is operatively coupled to the one or more first transducer elements in the ultrasound probe and drives the transmission of the ultrasound signal by the one or more first transducer elements in place of the driving circuit included in the ultrasound probe.

2. The ultrasound system of claim 1, wherein the driving circuitry in the docking station includes an oscillator that introduces less noise into the ultrasound signal than an oscillator in the driving circuitry of the ultrasound probe.

3. The ultrasound system of claim 2, wherein the oscillator in the ultrasound probe provides a reference frequency for synchronizing operation of the oscillator in the docking station.

4. The ultrasound system of claim 1 wherein the driving circuitry in the docking station is operatively coupled to the processing circuitry in the ultrasound probe to receive the control signal from the processing circuitry.

5. The ultrasound system of claim 1, wherein the power supply in the ultrasound probe is a first power supply, and wherein the circuitry in the docking station includes a second power supply that provides power for transmission of the ultrasound signal.

6. The ultrasound system of claim 5, wherein when the ultrasound probe is coupled to the docking station, the driving circuitry in the docking station electrically couples to the ultrasound probe via the electrical connector and uses the power provided by the second power supply to transmit the ultrasound signal in a continuous wave mode of operation.

7. The ultrasound system of claim 5, wherein the power provided by second power supply introduces less electrical noise into the ultrasound signal than power provided by the first power supply.

8. The ultrasound system of claim 5, wherein the second power supply is thermally coupled to a heat dissipation element that provides greater heat dissipation than a heat dissipation element thermally coupled to the first power supply.

9. The ultrasound system of claim 1, wherein the processing circuitry detects when the ultrasound probe is coupled to the docking station, and subsequent to detecting that the ultrasound probe is coupled to the docking station, the processing circuitry in the ultrasound probe controls the driving circuitry in the docking station such that the ultrasound probe transmits the ultrasound signal and receives echo signals in a continuous wave mode of operation.

10. The ultrasound system of claim 9, wherein the ultrasound probe further includes a user interface that receives a user actuation of the ultrasound probe, and when the ultrasound probe is coupled to the docking station, the user actuation determines whether the ultrasound probe transmits the ultrasound signal in the pulsed wave mode of operation or the continuous wave mode of operation.

11. The ultrasound system of claim 1, wherein the ultrasound probe comprises:
    a handheld transducer that includes at least the one or more first transducer elements and the one or more second transducer elements; and
    a computing device electrically coupled to the handheld transducer, the computing device including the power supply and at least a portion of the processing circuitry that controls transmission of the ultrasound signal from the one or more first transducer elements,
    wherein the docking station includes a first receiving section configured to hold at least a portion of the computing device when the ultrasound probe is coupled to the docking station.

12. The ultrasound system of claim 11, wherein the first receiving section includes a heat dissipating component that thermally couples to the computing device and conveys heat away from the computing device when the ultrasound probe is coupled to the docking station.

13. The ultrasound system of claim 11, wherein the docking station further includes a second receiving section configured to hold the handheld transducer.

14. The ultrasound system of claim 13, wherein the second receiving section includes a heat dissipating component that thermally couples to the handheld transducer and conveys heat away from the handheld transducer when the handheld transducer is placed in the second receiving section.

15. The ultrasound system of claim 1, wherein when the ultrasound probe is not coupled to the docking station, transmission of the ultrasound signal in a continuous wave mode of operation is limited to shorter periods of time than when the ultrasound probe is coupled to the docking station.

16. The ultrasound system of claim 1, wherein when the ultrasound probe is not coupled to the docking station, the ultrasound probe is configured to not transmit the ultrasound signal in a continuous wave mode of operation.

17. A docking station for use with a handheld ultrasound probe, the docking station comprising:
    an electrical connector couplable to a handheld ultrasound probe that is operable to transmit an ultrasound signal both when connected and when not connected to the docking station; and
    circuitry in the docking station that is electrically couplable to the ultrasound probe via the electrical connector and enhances transmission of the ultrasound signal by the ultrasound probe when the docking station is connected to the ultrasound probe, wherein the circuitry in the docking station includes driving circuitry and when the docking station is coupled to the ultrasound probe, the driving circuitry in the docking station drives the transmission of the ultrasound signal in place of driving circuitry of the ultrasound probe.

18. The docking station of claim 17, wherein the driving circuitry in the docking station includes an oscillator that introduces less noise into the ultrasound signal than an oscillator in the ultrasound probe.

19. The docking station of claim 18, wherein operation of the oscillator in the docking station is synchronized by a reference frequency provided by the oscillator in the ultrasound probe.

20. The docking station of claim 17, wherein the driving circuitry in the docking station is separate from the driving circuitry in the ultrasound probe, and when the docking station is coupled to the ultrasound probe, the driving circuitry in the docking station drives the transmission of a continuous wave ultrasound signal.

21. The docking station of claim 17, wherein the circuitry includes a power supply that provides power for driving the ultrasound signal when the docking station is coupled to the ultrasound probe.

22. The docking station of claim 21, wherein the power provided by the power supply of the docking station introduces less electrical noise into the ultrasound signal than power otherwise provided by a power supply in the ultrasound probe.

23. The docking station of claim 21, wherein, when the docking station is coupled to the ultrasound probe, the power provided by the power supply of the docking station drives the one or more transducer elements in the ultrasound probe to transmit a continuous wave ultrasound signal.

24. The docking station of claim 21, wherein the power supply is coupled to a heat dissipation element that provides greater heat dissipation than a heat dissipation element coupled to a power supply in the ultrasound probe.

25. The docking station of claim 17, further comprising a receiving section configured to hold at least a portion of the ultrasound probe when the docking station is coupled to the ultrasound probe.

26. The docking station of claim 25, wherein the receiving section includes a heat dissipating component that thermally couples to the ultrasound probe and conveys heat away from the ultrasound probe when the docking station is coupled to the ultrasound probe.

27. The docking station of claim 25, wherein the receiving section includes multiple receiving sections that are configured to hold different portions of the ultrasound probe when the docking station is coupled to the ultrasound probe.

28. The docking station of claim 17, further comprising processing circuitry that provides a greater computational resource than the ultrasound probe for processing an echo signal received in response to transmission of an ultrasound signal by the ultrasound probe.

29. The docking station of claim 17, further comprising one or more audio speakers having a better frequency response than audio speakers otherwise included in the ultrasound probe.

30. A method for transmitting an ultrasound signal from a handheld ultrasound probe, the method comprising:
positioning the ultrasound probe with respect to a target structure in a region of interest;
operating the ultrasound probe in a first mode of operation or a second mode of operation, wherein:
in the first mode of operation, one or more first transducer elements in the ultrasound probe transmit a pulsed wave ultrasound signal toward the target structure and one or more second transducer elements receive an echo signal returning from the target structure;
in the second mode of operation, the one or more first transducer elements in the ultrasound probe transmit a continuous wave ultrasound signal toward the target structure while the one or more second transducer elements receive echo signals returning from the target structure; and
coupling the ultrasound probe to a separate docking station having circuitry that enhances operation of the ultrasound probe in the first mode of operation or the second mode of operation by using driving circuitry in the docking station to drive the transmission of the ultrasound signal in line of driving circuitry in the ultrasound robe that otherwise drives the transmission of the ultrasound signal when the ultrasound prove is not coupled to the docking station.

31. The method of claim 30, wherein the circuitry in the docking station includes a power supply that provides quieter power for transmission of the ultrasound signal as compared to power provided by a power supply in the ultrasound probe that otherwise powers the transmission of the ultrasound signal when the ultrasound probe is not coupled to the docking station.

32. The method of claim 31, wherein the power provided by power supply in the docking station introduces less electrical noise into the ultrasound signal than the power provided by the power supply in the ultrasound probe.

33. The method of claim 31, further comprising coupling the power supply in the docking station to a heat dissipation element that provides greater heat dissipation than a heat dissipation element coupled to the power supply in the ultrasound probe.

34. The method of claim 31, further comprising:
detecting a docked state when the ultrasound probe is coupled to the docking station;
when the docked state is detected, controlling the circuitry in the docking station such that the ultrasound probe transmits the continuous wave ultrasound signal in the second mode of operation using power provided by the power supply in the docking station.

35. The method of claim 30, wherein coupling the ultrasound probe to the docking station comprises placing at least a portion of the ultrasound probe in a receiving section of the docking station, the receiving section including a heat dissipating component that thermally couples to ultrasound probe and conveys heat away from the ultrasound probe when the ultrasound probe is coupled to the docking station.

36. The method of claim 35, wherein the docking station includes at least a first receiving section that is separate from a second receiving section, the method further comprising placing the portion of the ultrasound probe in the first receiving section and placing another portion of the ultrasound probe in the second receiving section.

37. The method of claim 30, wherein the circuitry in the docking station includes driving circuitry with an oscillator that operatively couples to one or more transducer elements of the ultrasound probe when the ultrasound probe is coupled to the docking station, the method further comprising using the oscillator of the docking station when driving the transmission of the ultrasound signal in the first or second mode of operation.

38. The method of claim 37, wherein the oscillator introduces less noise into the ultrasound signal than an oscillator in the ultrasound probe that is otherwise used by the ultrasound probe when driving the ultrasound signal in an undocked state.

\* \* \* \* \*

UNITED STATES PATENT AND TRADEMARK OFFICE
CERTIFICATE OF CORRECTION

PATENT NO. : 10,667,787 B2
APPLICATION NO. : 15/446290
DATED : June 2, 2020
INVENTOR(S) : Ron Broad et al.

Page 1 of 1

It is certified that error appears in the above-identified patent and that said Letters Patent is hereby corrected as shown below:

In the Claims

Column 11, Claim 1, Line 39:
"driving circuit included"
Should be:
--driving circuitry included--.

Column 14, Claim 30, Line 21:
"signal in line of driving"
Should be:
--signal in place of driving--.

Column 14, Claim 30, Line 23:
"when the ultrasound prove is"
Should be:
--when the ultrasound probe is--.

Signed and Sealed this
Fifteenth Day of September, 2020

Andrei Iancu
*Director of the United States Patent and Trademark Office*